United States Patent [19]

Soodak

[11] 4,256,696
[45] Mar. 17, 1981

[54] CUVETTE ROTOR ASSEMBLY

[75] Inventor: Charles Soodak, Silver Spring, Md.

[73] Assignee: Baxter Travenol Laboratories, Inc., Deerfield, Ill.

[21] Appl. No.: 113,766

[22] Filed: Jan. 21, 1980

[51] Int. Cl.³ .............................................. G01N 21/07
[52] U.S. Cl. ........................................ 422/72; 233/26; 422/64
[58] Field of Search ....................... 422/72, 64; 233/26; 356/246

[56] References Cited

U.S. PATENT DOCUMENTS

| | | | |
|---|---|---|---|
| 3,555,284 | 1/1971 | Anderson | 422/72 X |
| 3,744,974 | 7/1973 | Maddox et al. | 422/72 |
| 3,890,101 | 6/1975 | Tiffany et al. | 422/72 X |
| 3,899,296 | 8/1975 | Mailen et al. | 422/72 X |
| 3,901,658 | 8/1975 | Burtis et al. | 422/72 X |
| 4,193,538 | 3/1980 | Schwarz | 422/72 X |

*Primary Examiner*—Ronald Serwin
*Attorney, Agent, or Firm*—R. A. Benziger; T. R. Vigil; P. C. Flattery

[57] ABSTRACT

The cuvette rotor assembly is adapted for use in a multi-station photometric analyzer of the type wherein several chemical reactions are sequentially monitored over a predetermined time span. Such an assembly includes a ring shaped cuvette rotor having an outer circular periphery, an inner circular periphery, a first side, a second side and cuvette forming slots extending between the sides and into the rotor from the inner periphery toward the outer periphery. A mixture of reagent and sample is urged by centrifugal force into the cuvette forming slots as the rotor is rotated. A fixed beam of light is directed at one side of the rotor as the rotor is rotating and the light that passes through each cuvette as a reaction is taking place therein is sensed and measured. The ring shaped cuvette rotor is made of a forged and age hardened chromium copper material and has a width between the inner and outer peripheries thereof sufficient to permit a hole to be drilled into the outer periphery for receiving a thermistor and sufficient to permit a flat ring of material to be secured to one side of the ring between the outer periphery and the inner ends of the slots.

10 Claims, 16 Drawing Figures

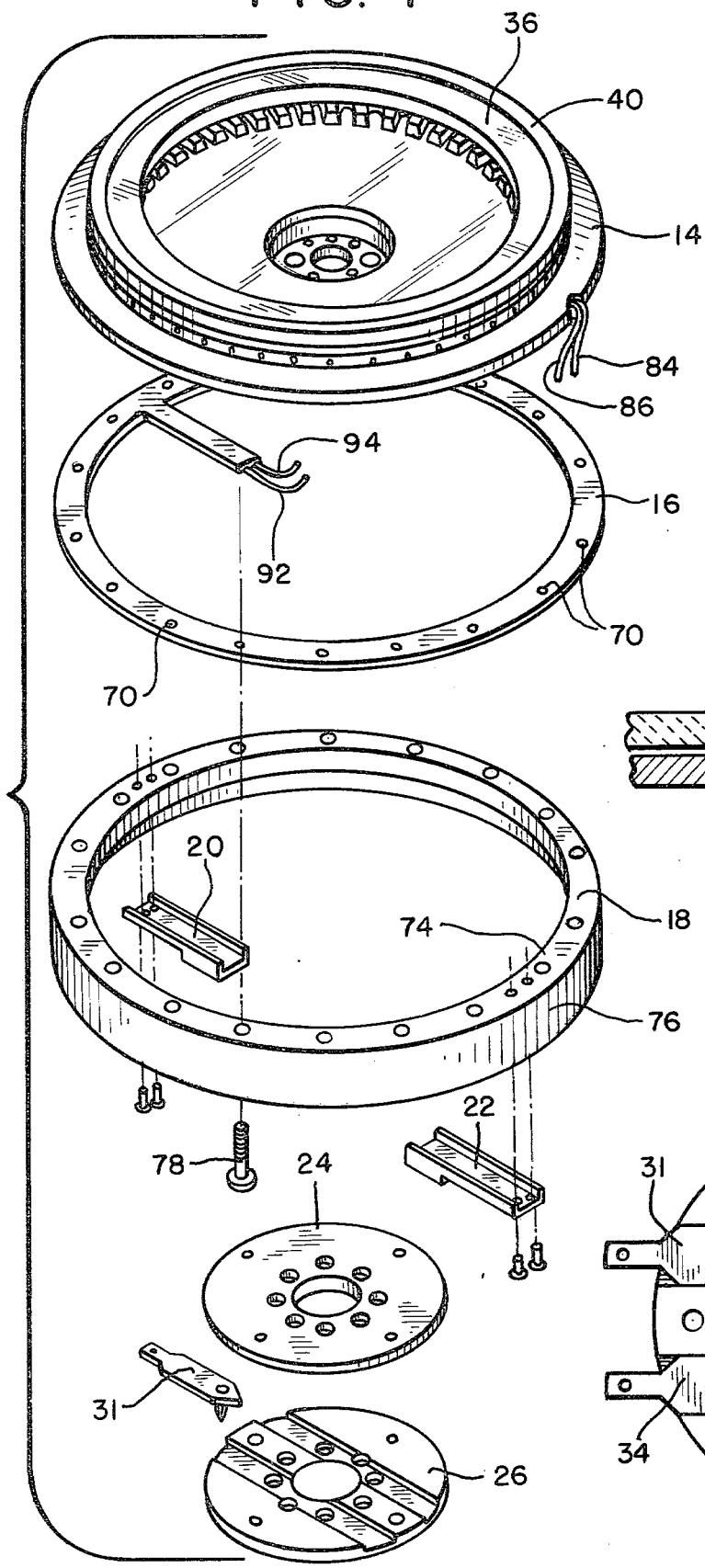
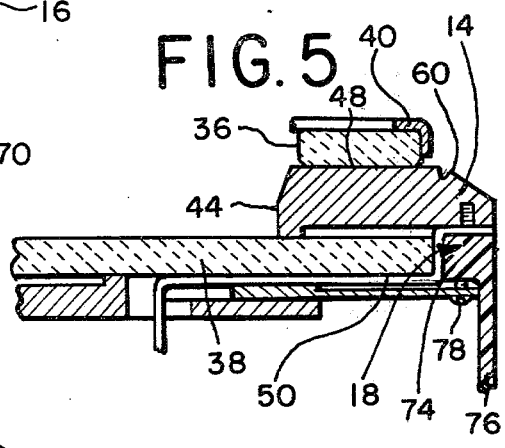
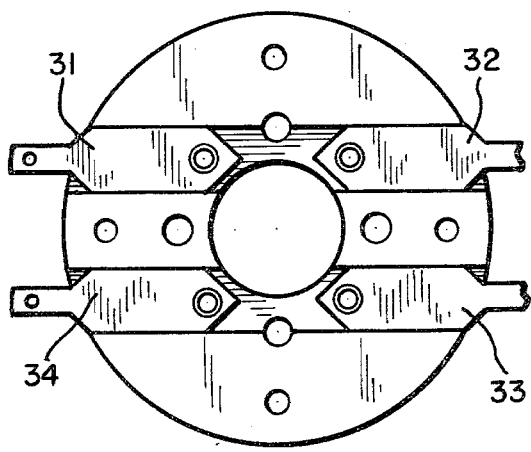

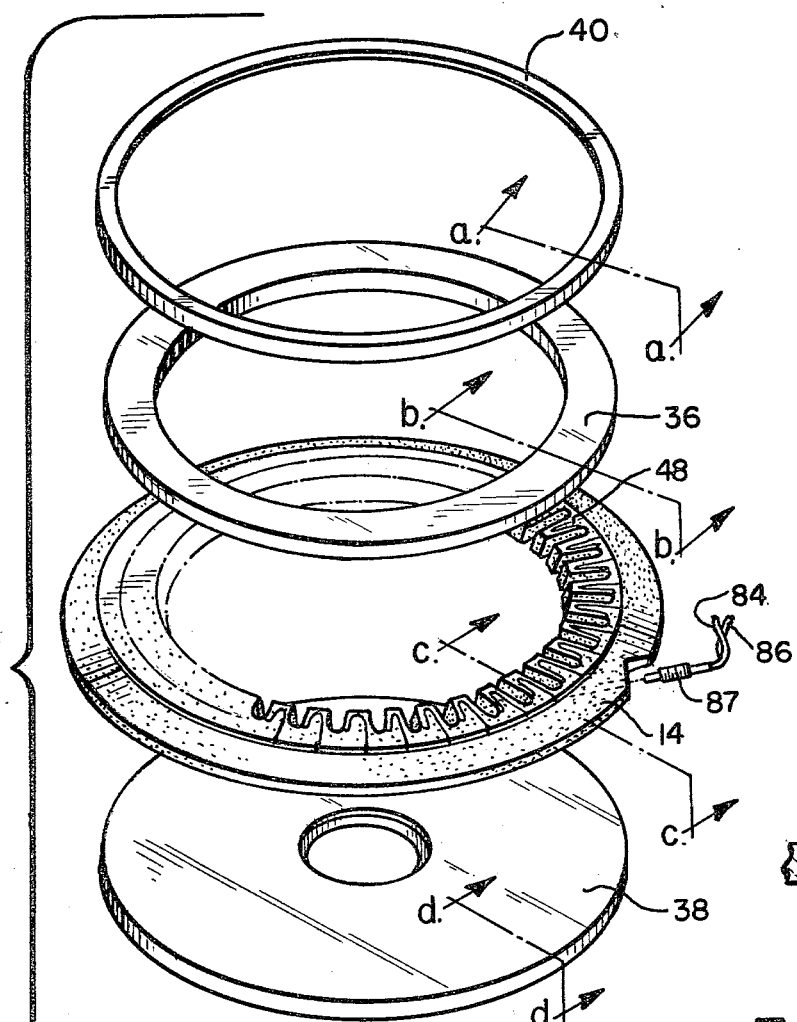
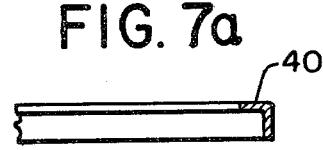
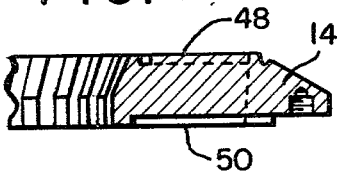
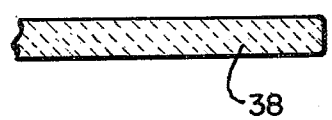
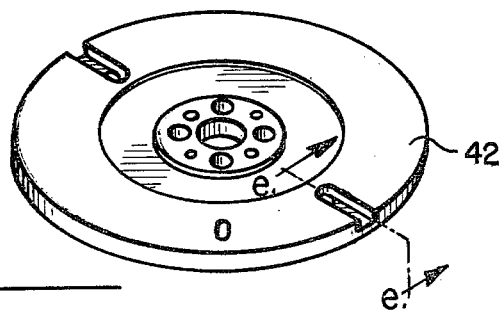
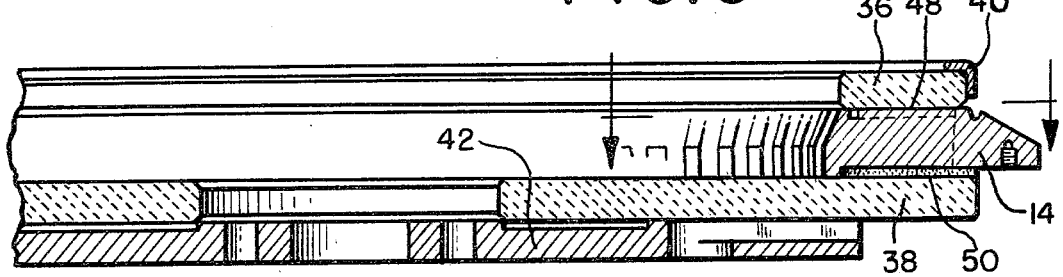

CUVETTE ROTOR ASSEMBLY

BACKGROUND OF THE INVENTION

1. Field of the Invention

The present invention relates to improvements in a cuvette rotor assembly utilized in a multistation photometric analyzer of the type wherein several chemical reactions are sequentially monitored over a predetermined time span. More specifically, the present invention is directed to an improved cuvette rotor used in the assembly.

2. Description of the Prior Art

Heretofore, multistation photometric analyzers of the type wherein several chemical reactions are sequentially monitored over a predetermined time span have been proposed. In such analyzers a central transfer disc having a plurality of spoke like channels therein with each channel having three wells, is situated within a ring shaped cuvette rotor having an outer circular periphery, an inner circular periphery, a first side, a second side and cuvette forming slots extending between the sides and into the rotor from the inner periphery toward the outer periphery. Glass windows are situated on either side of the cuvette rotor and a fixed beam of light is directed toward one side of the rotor through the windows and through the cuvettes.

The inner well in each channel in the transfer disc receives a reagent or a sample and the middle well receives sample or reagent. When a reaction between a reagent and a sample is to be monitored, the transfer disc and the cuvette rotor are rotated. Centrifugal force then urges the liquid in the inner well into the middle well and then both liquids are urged by centrifugal force into the outer well where they are mixed. Further, the centrifugal force then urges the mixed liquid from the outer mixing well into one of the cuvettes. Then, each time that particular cuvette passes the fixed beam of light, the light that passes through the cuvette as the reaction is taking place therein is sensed and measured.

Examples of photometric analyzers of the type described above are disclosed in the following U.S. Patents:

| U.S. Pat. No. | PATENTEE |
|---|---|
| 3,514,613 | Mashburn |
| 3,536,106 | Anderson |
| 3,547,547 | Anderson |
| 3,555,284 | Anderson |
| 3,582,218 | Anderson |
| 3,586,484 | Anderson |
| 3,856,470 | Cullis et al. |

In the Cullis et al. U.S. Pat. No. 3,856,470 referred to above, there is disclosed a rotor apparatus wherein an electric heating element is secured by an adhesive to a ring shaped cuvette rotor in order to heat the mixture of reagent and sample in the cuvettes to optimum temperature and to maintain the mixtures at that temperature during the reaction time.

The previously proposed cuvette rotors and cuvette rotor assemblies including same have functioned very well in enabling a photometric analyzer incorporating same to monitor reactions between a reagent and a sample over a predetermined time period. However, difficulties have been incurred in manufacturing the cuvette rotor and in the assembly including same. In this respect, a number of operations had to be performed on the cuvette rotor before it was ready for final assembly in a cuvette rotor assembly. This required shipping and handling of the rotor. Since the rotor was made of a soft copper material, the shipping and handling of the rotor as well as the various operations that were performed thereon often resulted in warping of the rotor and therefore rejection of same.

More specifically, the cuvette rotors heretofore utilized in photometric analyzers of the type sold under the trademark Rotochem by American Instrument Company of Silver Spring, Md., a Division of Baxter Travenol Laboratories, Inc., were made of solid "dead" copper, which is very soft material. Once the copper rotor was obtained from the manufacturer, it was sent out for machining. Then, when it came back from machining, it was sent out for nickel plating. After it was plated and returned, it was then sent out for securing a heating element thereto. It will be appreciated that the sending out of the cuvette rotor for coating, for finishing and for securing a heating element thereto, of necessity, required handling of the rotor which caused warping. Accordingly, each time the rotor was returned from an operation performed thereon, it had to be measured to see if it had warped.

Also, the previously utilized copper cuvette rotors did not provide a convenient means for monitoring the temperature of the rotor.

With a view toward overcoming these disadvantages incurred with the previously utilized copper cuvette rotors and as will be described in greater detail hereinafter, the present invention provides a cuvette rotor assembly including a cuvette rotor which is made of a harder copper alloy material and which is dimensioned so as to provide a cuvette rotor having a greater width between the inner and outer peripheries thereof. Also, the heating element is secured mechanically by fasteners so that the step of sending the cuvette rotor out for having an electric heating element secured thereto by an adhesive is eliminated.

SUMMARY OF THE INVENTION

According to the invention there is provided an improved cuvette rotor assembly for use in a multistation photometric analyzer of the type wherein several chemical reactions are sequentially monitored over a predetermined time span, wherein there is situated a ring shaped cuvette rotor having an outer circular periphery and an inner circular periphery, a first side and a second side and cuvette forming slots extending between the sides and into the rotor from the inner periphery toward the outer periphery and into which a mixture of reagent and sample is urged by centrifugal force as the rotor is rotating, and wherein a fixed beam of light is directed at one side of the rotor as the rotor is rotating and the light that passes through each cuvette as a reaction is taking place therein is sensed and measured, the improvement residing in said assembly including a ring shaped cuvette rotor made of forged and age hardened chromium copper material.

BRIEF DESCRIPTION OF THE DRAWINGS

FIG. 4 is an exploded perspective view of the cuvette rotor assembly except for the rotor subassembly.

FIG. 5 is a vertical sectional view of the cuvette rotor assembly.

FIG. 6 is a plan view of the connector supports for the connectors utilized to connect the heating element and the thermistor to slip ring connectors.

FIG. 7 is an exploded perspective view of the rotor subassembly.

FIGS. 7a–7e are vertical sectional views of the various parts of the rotor subassembly shown in FIG. 7.

FIG. 8 is a vertical sectional view of the rotor subassembly shown in FIG. 7.

DESCRIPTION OF THE PREFERRED EMBODIMENT

Figure 1:
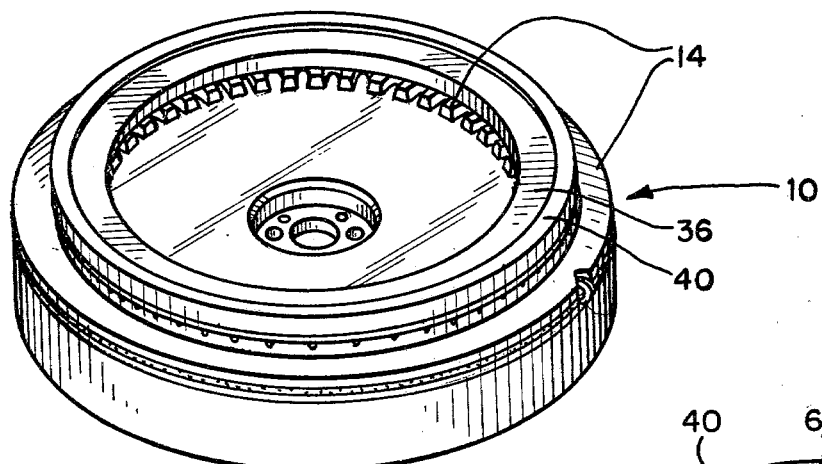
FIG. 1 is a perspective view of the cuvette rotor assembly of the present invention.
Figure 2:
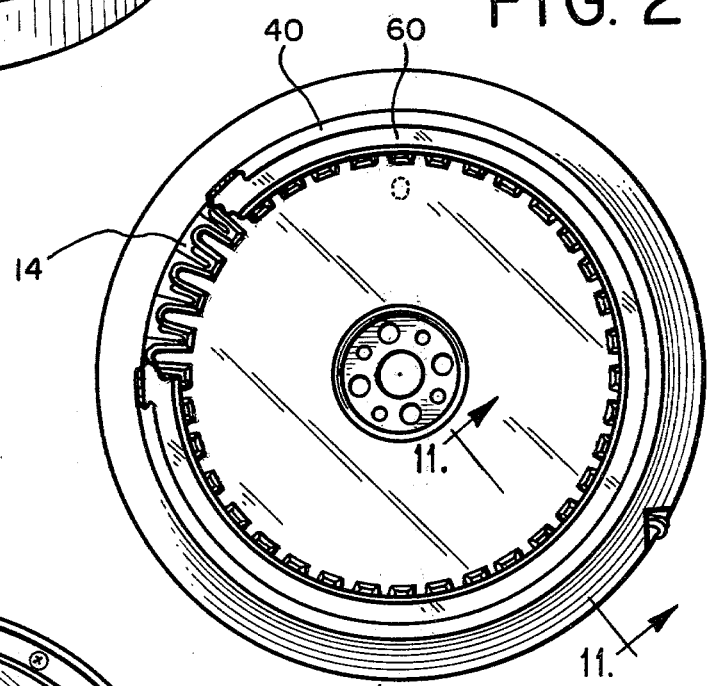
FIG. 2 is a top plan view of the rotor assembly shown in FIG. 1 with portions broken away.
Figure 3:
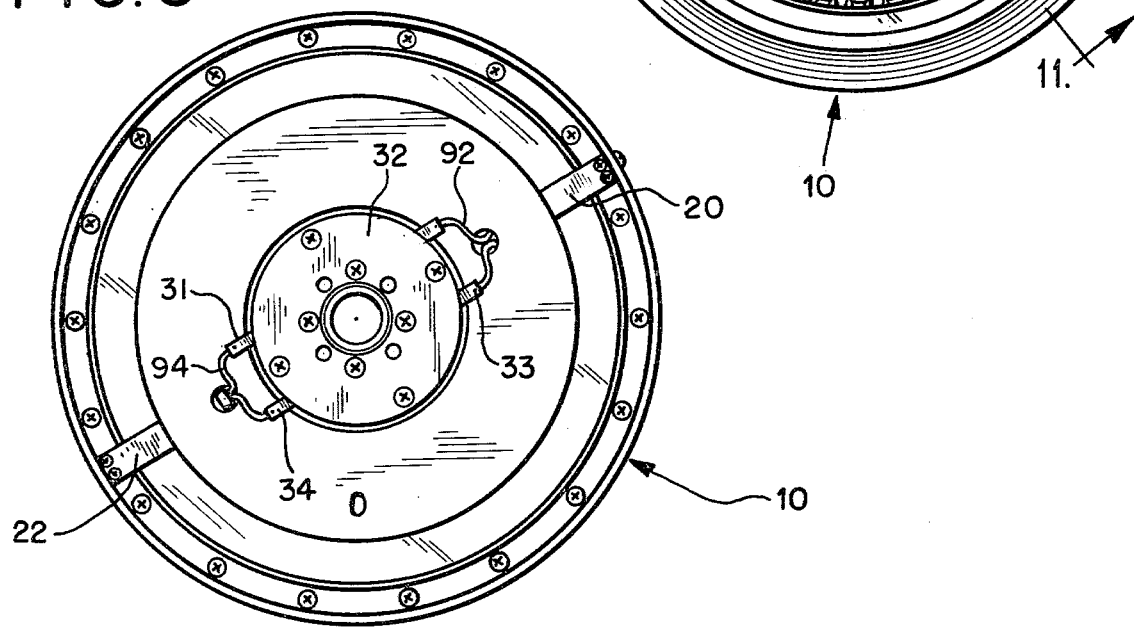
FIG. 3 is a bottom plan view of the rotor assembly shown in FIG. 1.

Referring now to the drawings in greater detail there is illustrated in FIG. 1 a perspective view of an assembled cuvette rotor assembly which is generally identified by the reference numeral 10. This rotor assembly 10 is utilized in a centrifugal chemical analysis apparatus of the type sold under the trademark 'Rotochem' by American Instrument Company of Silver Spring, Md., a Division of Baxter Travenol Laboratories, Inc., of Deerfield, Ill.

For further details on the construction and operation of the centrifugal chemical analysis apparatus, reference is made to U.S. Pat. No. 3,856,470, the disclosure of which is incorporated herein by reference.

The cuvette rotor assembly 10 includes a number of components which are shown in the various figures and which are exploded in two figures, namely FIGS. 4 and 7. In this respect FIG. 4 is an exploded view of the complete cuvette rotor assembly 10 which includes a rotor subassembly 12 including a rotor 14 (FIG. 7), a heating element 16, a plexiglass shield 18, first and second wire guides 20 and 22, and upper and lower connector supports 24 and 26 which mount therebetween four contact bars 31–34 with depending contact pins.

Turning now to FIGS. 7 and 7a–e, the rotor subassembly 12 includes not only the rotor 14 but also an upper clear glass quartz window 36, a lower clear glass quartz window 38, an upper guard ring 40 positioned on the upper window 36 and a drive flange 42 fixed adjacent the underside of the lower window 38.

Figure 9:
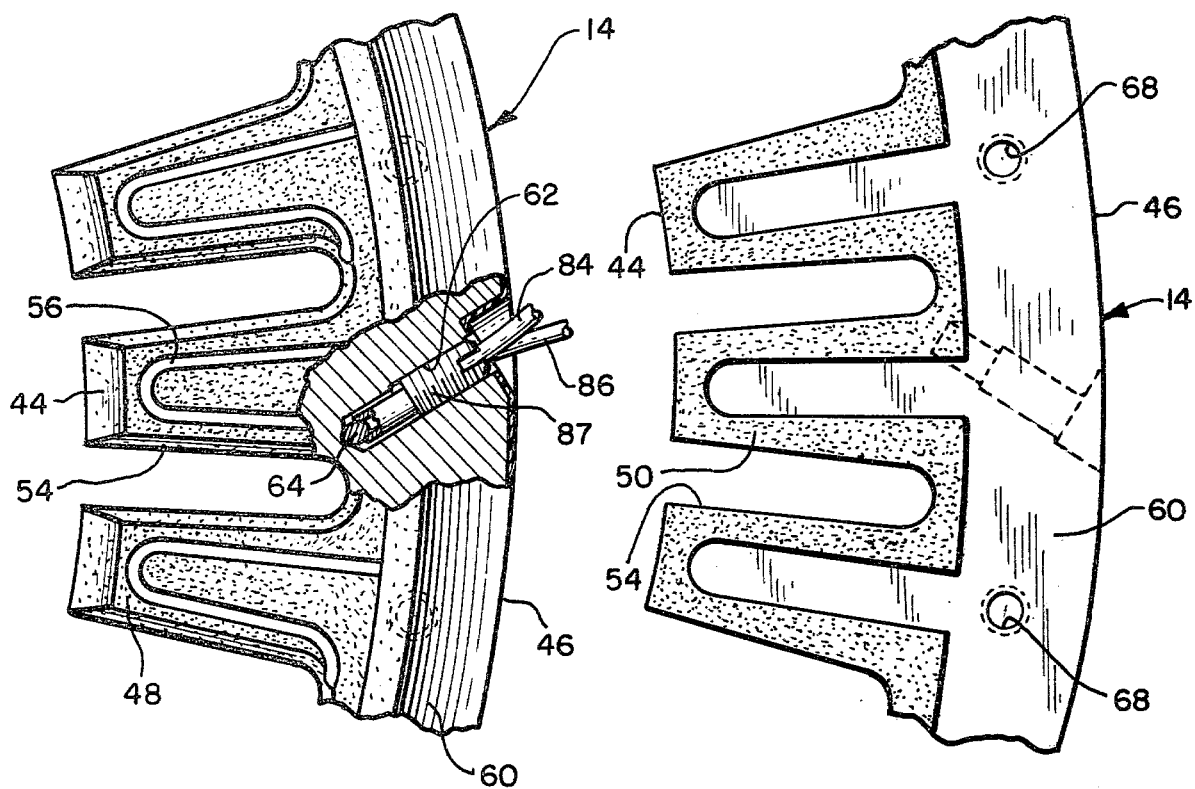
FIG. 9 is an enlarged fragmentary plan view of a portion of the cuvette rotor showing the thermistor mounted therein.
Figure 10:
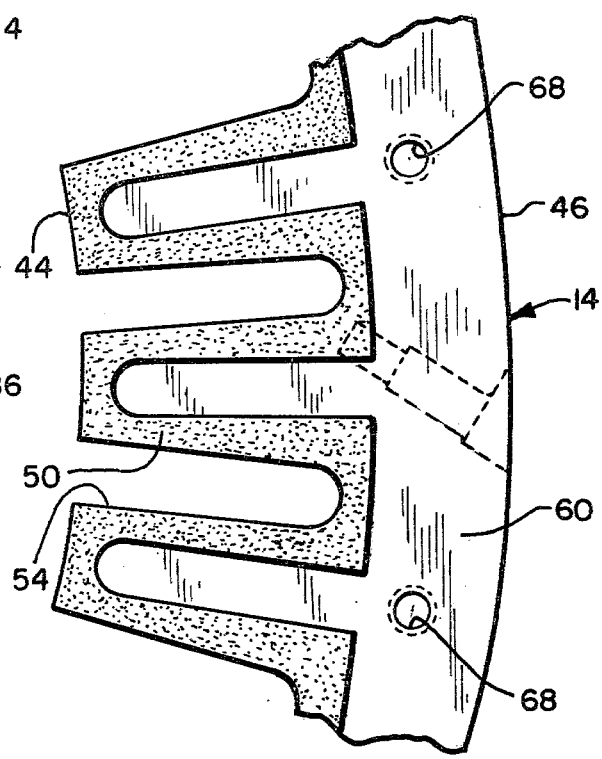
FIG. 10 is an enlarged fragmentary view of a portion of the cuvette rotor similar to the view shown in FIG. 9 but looking at the rotor from the other side thereof.
Figure 11:
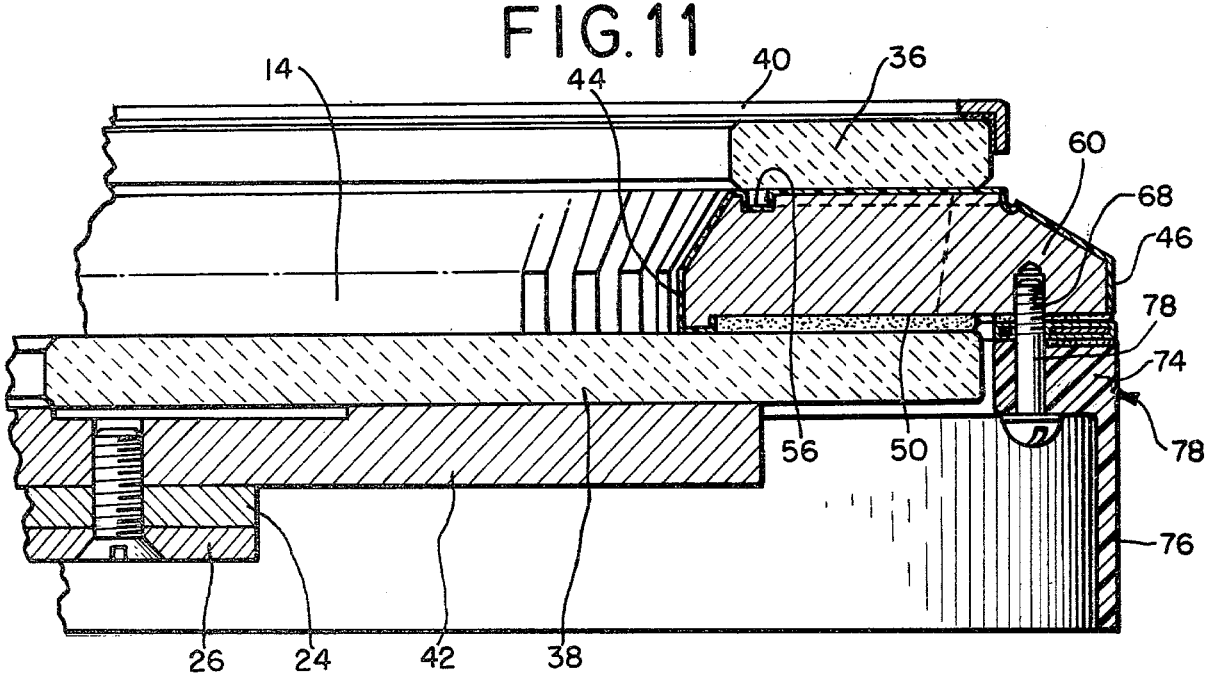
FIG. 11 is a fragmentary vertical sectional view of the cuvette rotor assembly.

As shown in FIGS. 9, 10 and 11, the cuvette rotor 14 has a generally flat ring shape or annular shape like a large thick washer such that the cuvette rotor 14 has an inner circular periphery 44, and outer circular periphery 46, an upper side 48 and a lower side 50. As best shown in FIGS. 9 and 10, a plurality of cuvette forming slots 54 are formed in the rotor 14 with each slot extending between the upper and lower sides 48 and 50 and into the rotor 14 from the inner periphery 44 thereof toward but not to the outer periphery 46. These slots 54 form cuvettes into which a liquid mixture of sample and reagent is urged when the rotor assembly 10 is rotated with a transfer disc (not shown) which is seated in the rotor assembly 10.

The reactions that take place within the cuvettes 54 are monitored by directing a fixed beam of light from beneath the rotor assembly 10 through the lower glass window 38, the cuvette 54 and the upper glass window 36 to a photosensitive device (not shown).

As best shown in FIG. 9, the area of the upper side 48 of the rotor between each pair of adjacent slots 54 has a specially configured groove 56 formed therein. This groove facilitates the siphoning out of liquid from the cuvettes 54 after the reactions have been completed.

As shown in FIG. 10, the area on the underside 50 of the rotor 14 adjacent the cuvettes 54 extends slightly further downwardly than the remainder of the underside 50 of the rotor which is relieved. This is done so that there is a good seal provided between the lower window 38 in the area adjacent the slots/cuvettes 54.

In accordance with the teachings of the present invention, the rotor 14 has a coating of polyvinylidene difluoride as best shown in FIG. 11. The polyvinylidene difluoride can be of the type sold under the trademark "Kynar". This material is very inert with respect to the chemical reactions that take place in the cuvettes 54 and ensures that no part of the coating is involved in the reaction which takes place in the cuvettes 54 and prevents any of the metal out of which the rotor 14 is made from entering into the liquid solutions in the cuvettes 54. If desired, the rotor 14 can also be plated with an electroless nickel.

In order to increase the strength of the rotor 14 and in accordance with the teachings of the present invention, the rotor 14 is made of forged and age hardened chromium copper material sold under the tradename Ampcoloy 97 by Ampco Metal of Philadelphia, Pa.

Further according to the teachings of the present invention, the width of the rotor between the inner periphery 44 and outer periphery 46 thereof is increased from previous rotors. In this respect, the rotor 14 is made sufficiently wide between the inner and outer peripheries 44 and 46 thereof to provide a volume of material generally identified by the reference numeral 60. In this respect, the rotor 14 of the present invention has an additional radius of approximately 0.25 inches (0.635 cm) over existing rotors.

This greater thickness in the width of the rotor 14 not only increases the strength of the rotor 14 to prevent warping of the rotor 14 but also permits a thermistor to be mounted in the rotor 14 as best shown in FIG. 9. In this respect, a countersunk bore 62 is drilled into the outer periphery 46 of the rotor 14 for receiving a thermistor 64.

Also, another advantage obtained by providing the greater thickness in the width of the rotor 14 is that instead of sending the rotor 14 out to a supplier to have a heating element secured to the underside 50 thereof by an adhesive, an annular, flat, ring shaped heating element such as the heating element 16 can be secured to the underside of the rotor 14 in the area between the inner ends of the slots 54 and the outer periphery 46 as best shown in FIGS. 4 and 11. In this respect, the rotor 14 has a plurality, namely 18, threaded bores 68 formed therein extending into the underside 50 in the area adjacent the outer periphery 46. As best shown in FIG. 4, the heating element 16 is provided with a plurality, namely 18, of holes 70 which are adapted to mate with the threaded bores 68. Then, the shield 18 is provided with an inwardly extending circular flange portion 74 and a lower depending cylindrical skirt portion 76 with the flange portion 74 having a plurality, namely 18, of holes 80 which mate with the holes 70 in the ring and the holes 68 in the rotor 14. Then a plurality, namely 18, of fasteners 78 are received through the holes 80 in the flange portion through the holes 70 in the heating element 16 and into the threaded bores 68 of the rotor 14 for securing the heating element 16 to the underside 50 of the rotor 14 between the flange portion 74 of the shield 18 and the underside 50. The shield 18 is made of polymethylmethacrylate.

In this way, the heating element 16 can be easily and mechanically secured to the rotor 14. With this assembly, if the heating element 16 should ever become defective, it is a very simple matter to replace the heating element 16 without replacing the whole rotor 14.

The depending skirt portion 76 of the shield 18 is provided in case any liquid should somehow work its way by gravity beneath the lower window 38 and lower connector support 26 and then be urged by centrifugal force outwardly of the rotor assembly 10. If this should occur, such liquid will hit the inner surface of the cylindrical skirt portion 76 and will be prevented from coming in contact with other portions of the centrifugal chemical analysis apparatus.

As shown in FIGS. 7 and 7a, the rotor subassembly 12 includes the guard ring 40 which has an L shaped cross section so that the guard ring 40 can be received over the upper outer corner of the ring shaped upper window 36 and protect the upper outer corner of the upper window 36 from being chipped during handling of the rotor assembly 10.

The four connectors 31-34 are supported in slots on the lower connector support 26 with pins extending therethrough for making slip ring connections. The upper connector support 24 is received over the lower connector support 26 and both supports are made of an insulating material. The connector supports are then secured to the underside of the drive flange 42 and the wire guides 22 and 20 are secured by fasteners through the flange portion 74 of the shield 18 to the rotor 14. In this way, wire conductors 84 and 86 from the thermistor 64 can extend through a hollow screw 87, which is secured in the base 62 to hold thermistor 64 in place, and then along the upper surface of the wire guide 22 and then extend through holes in the upper connector support 24 for connection to two of the connectors 31-34. Likewise wire conductors 92 and 94 from the heating element 16 can be received in the upper surface of the wire guide 20 and then through holes in the upper connector support 24 for connection to the other two of the connectors 31-34.

The rotor assembly 10 comprising the novel rotor 14, heating element 16, shield 18 and guard ring 40 provides an improved rotor assembly for use in a centrifugal chemical analysis apparatus of the type sold under the trademark 'Rotochem'. Such an improved assembly having the new and improved component parts described above has a number of advantages, some of which have been described above and others of which are inherent in the invention. Primarily, the new rotor assembly 10 provides a stronger rotor 14 which is less susceptible to warping. Also, the construction of the rotor assembly 10 is such that fewer outside operations are required on the rotor 14 thereby reducing the chances of the rotor 14 being damaged in handling. Moreover the clamping of the heating element 16 between the shield 18 and the underside 50 of the rotor 14 provides a simple manner for heating the rotor 14 and enables one to replace a defective heating element 16 without replacing the rotor 14.

Further in view of the foregoing description, it will be apparent that obvious modifications can be made to the new and improved rotor assembly 10 without departing from the teachings of the present invention. Accordingly, the scope of the invention is only to be limited as necessitated by the accompanying claims.

I claim:

1. An improved cuvette rotor assembly for use in a multistation photometric analyzer of the type wherein several chemical reactions are sequentially monitored over a predetermined time span, wherein there is situated a ring shaped cuvette rotor having an outer circular periphery and an inner circular periphery, a first side and a second side and cuvette forming slots extending between the sides and into the rotor from the inner periphery toward the outer periphery and into which a mixture of reagent and sample is urged by centrifugal force as the rotor is rotating, and wherein a fixed beam of light is directed at one side of the rotor as the rotor is rotating and the light that passes through each cuvette as a reaction is taking place therein is sensed and measured, the improvement residing in said assembly including a ring shaped cuvette rotor made of forged and age hardened chromium copper material.

2. The cuvette rotor assembly according to claim 1 wherein said cuvette rotor has a coating of polyvinylidene difluoride.

3. The cuvette rotor assembly according to claim 1 wherein said cuvette rotor has sufficient width to permit a hole to be drilled into the outer periphery thereof and wherein said assembly includes a thermistor received in a hole in the outer periphery of said rotor.

4. The cuvette rotor assembly according to claim 1 wherein said cuvette rotor has sufficient width to permit a flat ring of material to be secured to one side thereof between the inner ends of the cuvette forming slots and the outer periphery and wherein said assembly includes a flat ring shaped electric heating element structure secured to said one side.

5. The cuvette rotor assembly according to claim 4 wherein said assembly includes a collar of insulating material which is positioned against said heating element structure and wherein said assembly includes a plurality of fasteners received through holes in said collar and fastened in mating holes in said cuvette rotor.

6. The cuvette rotor assembly according to claim 4 wherein said assembly includes a shield member comprising a cylindrical skirt portion and a circular flat flange integral with and extending inwardly of said skirt portion, wherein said flange is positioned against said heating element structure and wherein said assembly includes a plurality of fasteners received through holes in said flange and fastened in mating holes in said cuvette rotor.

7. The cuvette rotor assembly according to claim 6 wherein said shield member is made of polymethylmethacrylate.

8. The cuvette rotor assembly according to claim 1 including first and second ring shaped glass windows situated, respectively, adjacent said first and second sides of said cuvette rotor and a circular guard ring having an inverted L shaped cross section and being situated on the outer corner edge of said first window to protect same from being chipped.

9. The cuvette rotor assembly according to claim 1 wherein said cuvette rotor has an outer diameter of approximately 9.13 inches (23.2 cm) and an inner diameter of approximately 6.41 inches (16.3 cm).

10. The cuvette rotor assembly according to claim 1 wherein said cuvette rotor has a thickness of approximately 0.387 inches (0.983 cm).

* * * * *